(12) United States Patent
Hagen et al.

(10) Patent No.: US 11,304,810 B2
(45) Date of Patent: Apr. 19, 2022

(54) IMPLANT AND JOINT IMPLANT

(71) Applicant: Aesculap AG, Tuttlingen (DE)

(72) Inventors: Thomas Hagen, Tuttlingen (DE);
Thomas Grupp, Denkingen (DE);
Thomas Schulz, Schmoelln-Putzkau (DE); Sacha T. W. Mann, Fernwald (DE)

(73) Assignee: Aesculap AQ, Tuttlingen (DE)

( * ) Notice: Subject to any disclaimer, the term of this patent is extended or adjusted under 35 U.S.C. 154(b) by 0 days.

(21) Appl. No.: 16/256,016

(22) Filed: Jan. 24, 2019

(65) Prior Publication Data

US 2019/0151102 A1    May 23, 2019

Related U.S. Application Data

(63) Continuation of application No. PCT/EP2017/069258, filed on Jul. 31, 2017.

(30) Foreign Application Priority Data

Jul. 29, 2016    (DE) .................... 10 2016 114 059.7

(51) Int. Cl.
*A61F 2/38*    (2006.01)
*A61F 2/30*    (2006.01)
(Continued)

(52) U.S. Cl.
CPC ............ *A61F 2/30767* (2013.01); *A61F 2/38* (2013.01); *A61F 2/389* (2013.01); *A61F 2/3859* (2013.01); *A61F 2/28* (2013.01); *A61F 2/3094* (2013.01); *A61F 2/32* (2013.01); *A61F 2/3886* (2013.01); *A61F 2002/30321* (2013.01); *A61F 2002/30324* (2013.01); *A61F 2002/30685* (2013.01); *A61F 2002/30976* (2013.01); *A61F 2002/3863* (2013.01); *A61F 2220/0008* (2013.01); *A61F 2310/00023* (2013.01);
(Continued)

(58) Field of Classification Search
CPC .... A61F 2002/30838–3084; A61F 2002/3093; A61F 2310/00407; A61F 310/00796
See application file for complete search history.

(56) References Cited

U.S. PATENT DOCUMENTS 4,209,861 A    7/1980    Walker et al.
4,213,209 A    7/1980    Insall et al.
(Continued)

FOREIGN PATENT DOCUMENTS

CA    2533534    2/2005
CN    101617969    1/2010
(Continued)

*Primary Examiner* — Rebecca S Preston
(74) *Attorney, Agent, or Firm* — Lipsitz & McAllister, LLC

(57) ABSTRACT

The invention relates to an implant with a shank which is insertible into a bone cavity, which shank is made of a plastic, in particular of a bioincompatible plastic, and defines at least one bone contact face, wherein the bone contact face is provided or coated with a first biocompatible bone contact layer or bears a biocompatible bone contact layer, wherein the shank of the implant is intended to be anchored in the bone cavity without bone cement and wherein the first bone contact layer is formed entirely closed.

16 Claims, 4 Drawing Sheets

Figure 1:
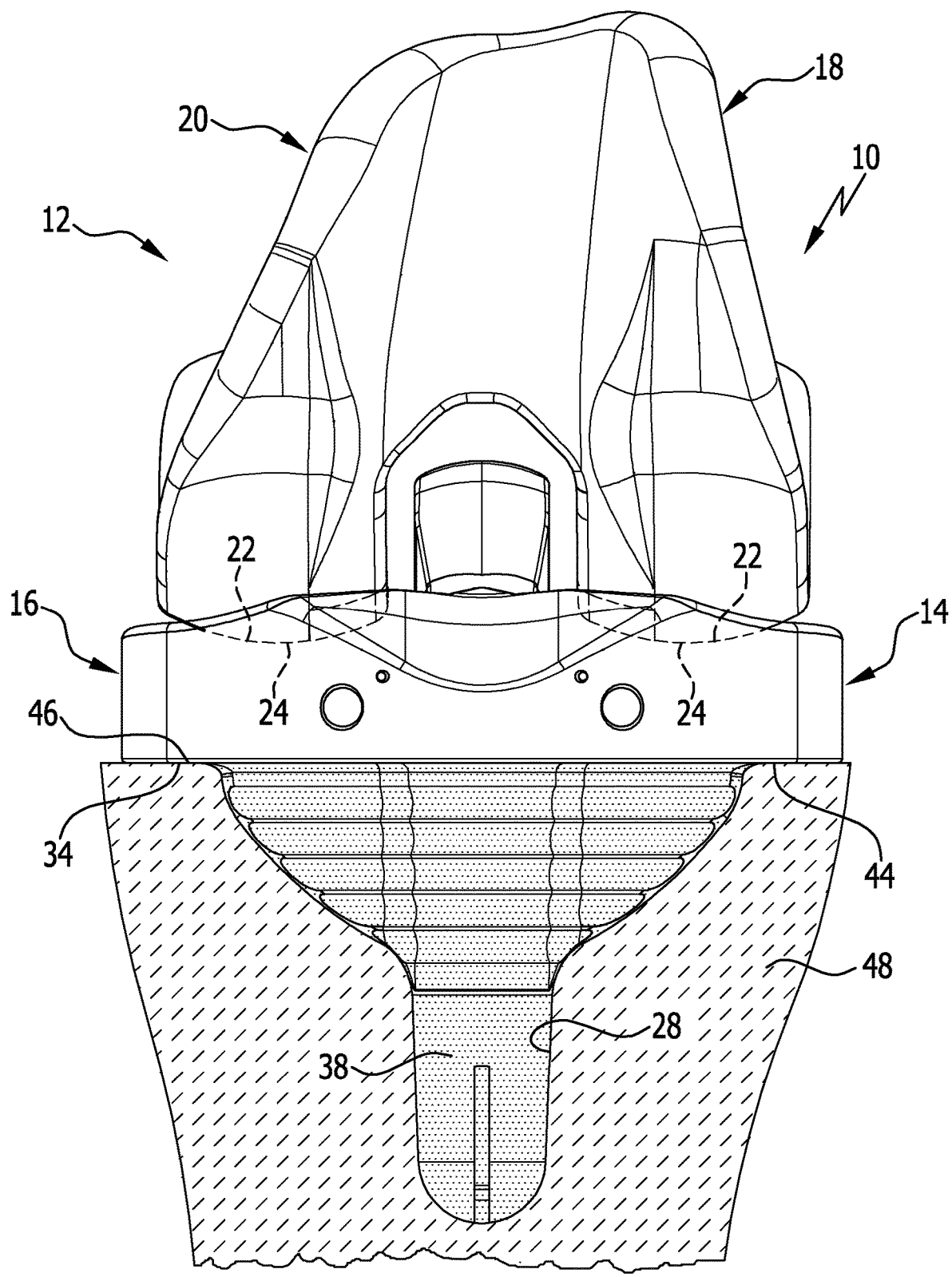

(51) Int. Cl.
   *A61F 2/32*     (2006.01)
   *A61F 2/28*     (2006.01)
   *A61L 27/34*    (2006.01)

(52) U.S. Cl.
   CPC ............. *A61F 2310/00395* (2013.01); *A61F 2310/00407* (2013.01); *A61F 2310/00796* (2013.01); *A61F 2310/00958* (2013.01); *A61L 27/34* (2013.01)

(56) References Cited

U.S. PATENT DOCUMENTS

| | | | |
|---|---|---|---|
| 4,298,992 A | 11/1981 | Burstein et al. | |
| 5,509,934 A | 4/1996 | Cohen | |
| 2007/0224242 A1 | 9/2007 | Helmuth et al. | |
| 2009/0177282 A1* | 7/2009 | Bureau | C23C 4/12 623/16.11 |
| 2010/0211180 A1 | 8/2010 | Helmuth et al. | |
| 2010/0249784 A1* | 9/2010 | Andersson | H04R 25/606 606/76 |
| 2011/0009964 A1* | 1/2011 | Schwartz | A61F 2/4684 623/14.12 |
| 2012/0109324 A1 | 5/2012 | Keggi et al. | |
| 2012/0116524 A1* | 5/2012 | Walker | A61B 17/157 623/20.35 |
| 2012/0330429 A1* | 12/2012 | Axelson, Jr | A61F 2/30771 623/20.19 |
| 2013/0218284 A1* | 8/2013 | Eickmann | A61F 2/389 623/20.34 |
| 2013/0302512 A1* | 11/2013 | McEntire | A61L 27/50 427/2.26 |
| 2018/0116807 A1* | 5/2018 | Lenich | A61F 2/30771 |

FOREIGN PATENT DOCUMENTS

| | | |
|---|---|---|
| CN | 102014800 | 4/2011 |
| CN | 105030379 | 11/2015 |
| DE | 2906458 | 8/1979 |
| DE | 4102256 | 7/1992 |
| EP | 1133957 | 9/2001 |
| JP | 2008513120 | 5/2008 |
| JP | 201192740 | 5/2011 |
| JP | 2014176686 | 9/2014 |
| WO | 2015133913 | 9/2015 |

* cited by examiner

IMPLANT AND JOINT IMPLANT

CROSS-REFERENCE TO RELATED APPLICATIONS

This application is a continuation of international application number PCT/EP2017/069258 filed on Jul. 31, 2017 and claims the benefit of German application number 10 2016 114 059.7 filed on Jul. 29, 2016, which are incorporated herein by reference in their entirety and for all purposes.

FIELD OF THE INVENTION

The present invention relates to implants generally, and more specifically to an implant with a shank which is insertible into a bone cavity, which shank is made of a bioincompatible plastic and defines at least one bone contact face.

Further, the present invention relates to joint implants generally, and more specifically to a joint implant with a first joint component and at least one second joint component cooperating with the first joint component.

BACKGROUND OF THE INVENTION

Joint implants of the kind stated at the outset are used, e.g., in the form of knee joint endoprostheses in order to replace degenerate or deformed knee joints of humans. Such a knee joint endoprosthesis comprises at least two joint components, namely a tibial component and a femoral component which cooperate with each other for forming an artificial knee joint. The two joint components are hereby in particular configured in the form of an implant of the kind described at the outset.

For example, known from U.S. Pat. No. 4,209,861 is a knee joint endoprosthesis with a tibial component which is made entirely of a plastic, for example a high density polymer like UHMWPE.

In the last decades, it has proven that implants made of plastic, in particular implants made of UHMWPE, should not come into direct contact with bone. UHMWPE is a hydrophobic material and thus offers very unfavorable conditions for bone tissue to grow into the surface of the implant. Micromovements thus persistently occur at the boundary face between bone tissue and the surface of the implant, which may lead to a connective tissue deformation and to a degradation of the plastic on the implant. In order to avoid this problem, tibial components of knee joint endoprostheses which are made entirely of a plastic are fixed with bone cement. A cement mantle or a cement layer, respectively, hereby forms between the bone contact face of the implant and the bone tissue. The bone cement thus serves, on the one hand, for fixing the implant in and on the bone, respectively, and simultaneous also as a separating layer between the plastic and the bone tissue.

A problem in the cementing of shanks of tibial components which are made entirely of plastic is that it could result in stress peaks at the end of the shank. These do not occur in an implantation of the tibial component which in the shank region is not cemented in. In the worst case, the described stress peaks may lead to a break of the tibia, i.e., of the bone surrounding the shank.

SUMMARY OF THE INVENTION

In a first aspect of the invention an implant with a shank is provided. The shank is insertible into a bone cavity. The shank is made of a plastic, in particular of a bioincompatible plastic, and defines at least one bone contact face. The bone contact face is provided or coated with a first biocompatible bone contact layer or bears a biocompatible bone contact layer. The shank of the implant is intended to be anchored in the bone cavity without bone cement. The first bone contact layer is formed entirely closed.

In a second aspect of the invention, a joint implant with a first joint component and at least one second joint component cooperating with the first joint component is provided. The first joint component and/or the at least one second joint component are configured in the form of an implant with a shank. The shank is insertible into a bone cavity. The shank is made of a plastic, in particular of a bioincompatible plastic, and defines at least one bone contact face. The bone contact face is provided or coated with a first biocompatible bone contact layer or bears a biocompatible bone contact layer. The shank of the implant is intended to be anchored in the bone cavity without bone cement. The first bone contact layer is formed entirely closed.

BRIEF DESCRIPTION OF THE DRAWING FIGURES

Figure 2:
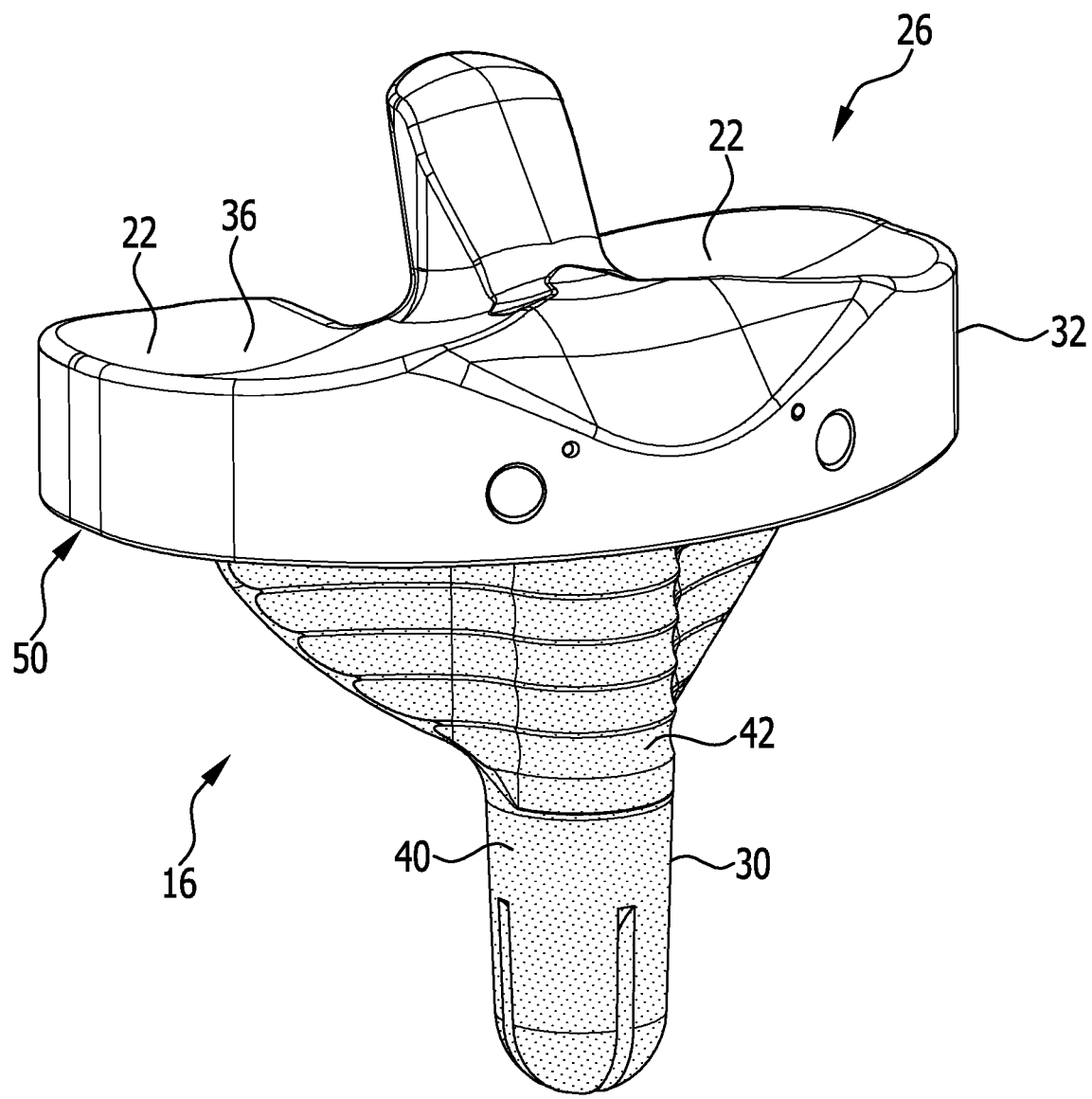
Figure 3:
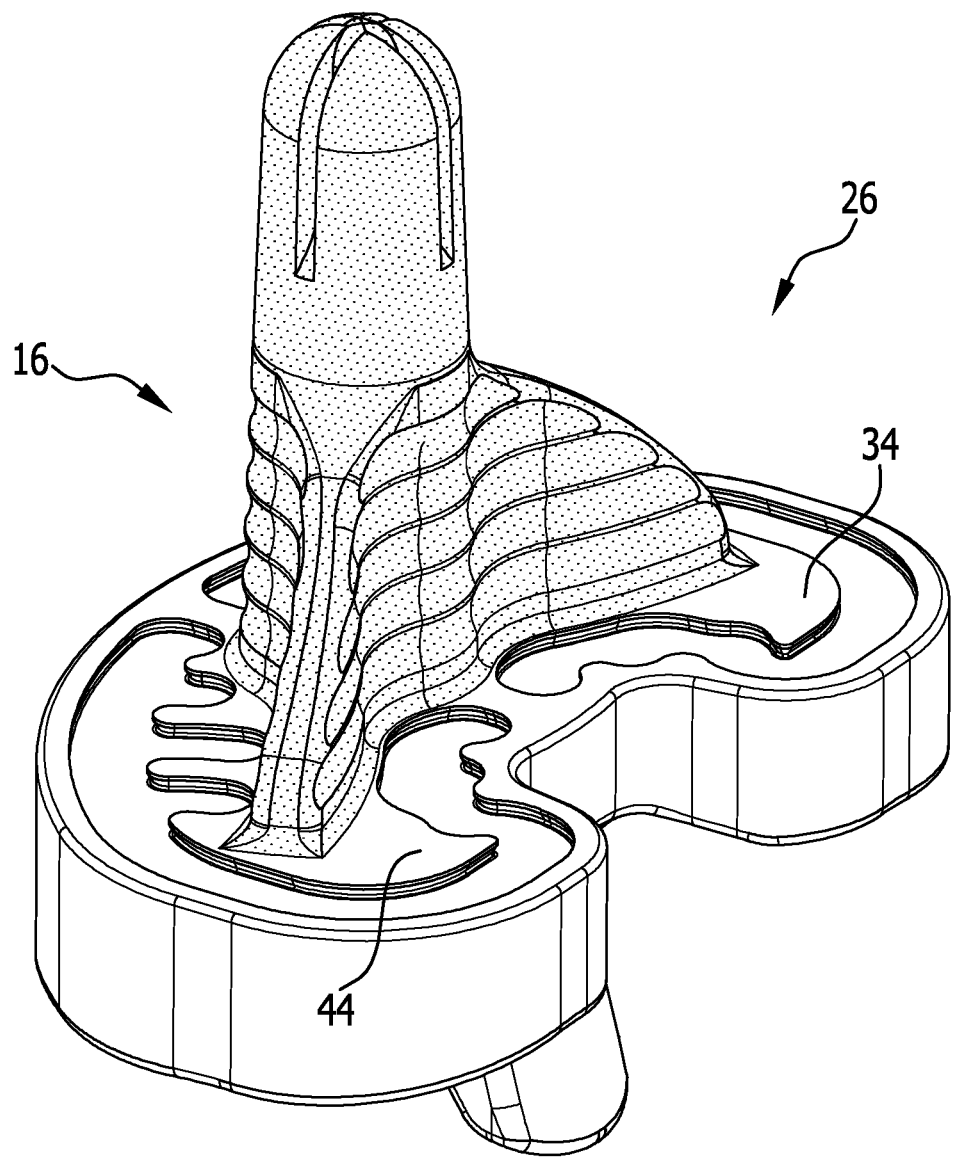
Figure 4:
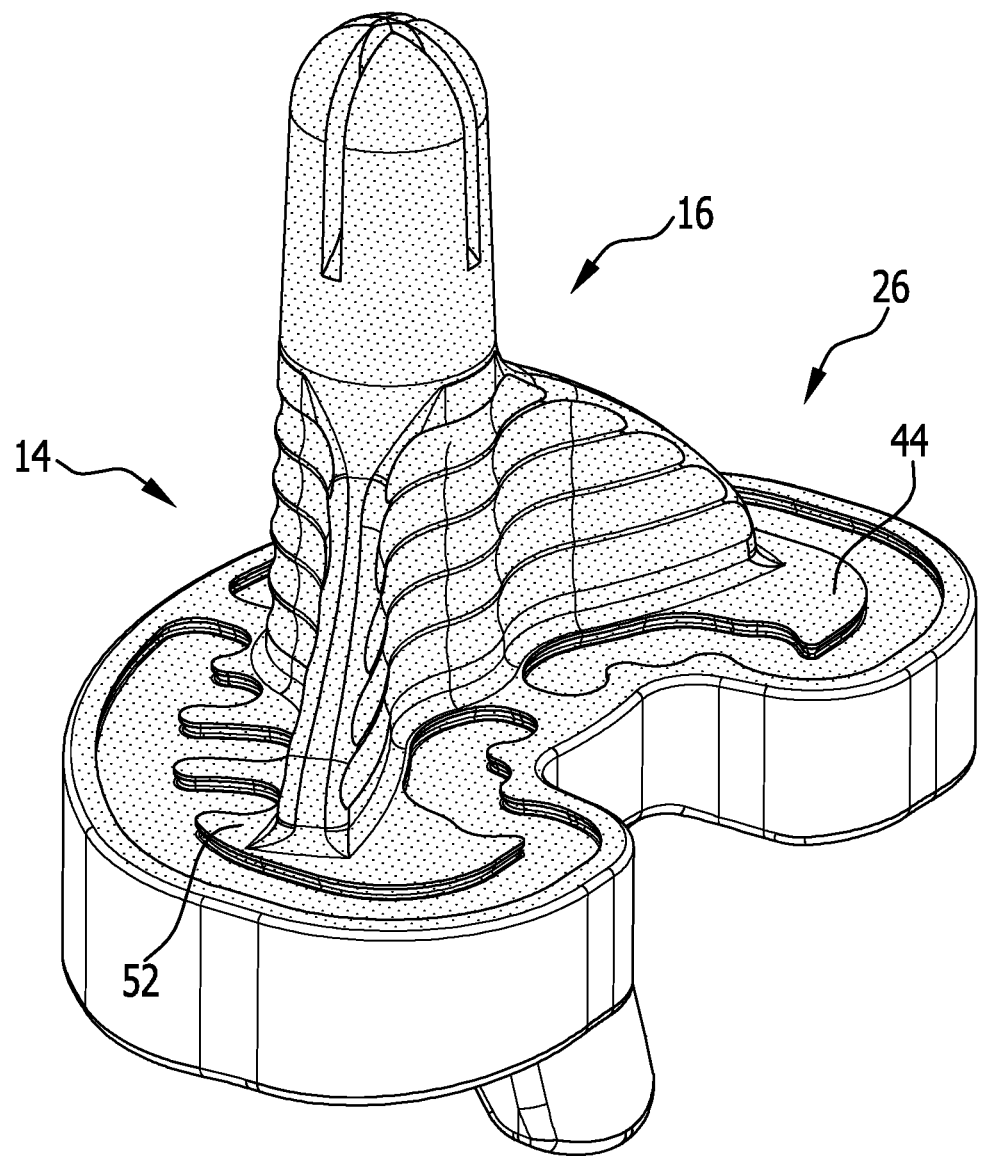

The foregoing summary and the following description may be better understood in conjunction with the drawing figures, of which:

FIG. 1: shows a side view of a joint implant in the form of a knee joint endoprosthesis;

FIG. 2: shows a perspective view of the tibial component of the knee joint endoprosthesis depicted in FIG. 1;

FIG. 3: shows a further perspective view of the tibial component from FIG. 2; and FIG. 4: shows a further embodiment of a tibial component of a knee joint endoprosthesis.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to an implant with a shank which is insertible into a bone cavity, which shank is made of a plastic, in particular of a bioincompatible plastic, and defines at least one bone contact face, wherein the bone contact face is provided or coated with a first biocompatible bone contact layer or bears a biocompatible bone contact layer, wherein the shank of the implant is intended to be anchored in the bone cavity without bone cement and wherein the first bone contact layer is formed entirely closed.

The proposed further development of a known implant enables in particular fixing the latter on or in a bone without the use of bone cement. In particular, the shank, the at least one bone contact face of which is provided or coated with the first biocompatible bone contact layer or bears the same, is brought into contact directly with bone or bone tissue, without the undesired consequences described above occurring. One may thus in particular dispense with the cementing of the shank, such that also the stress peaks described above do not occur, and the risk of a break of the tibia is significantly reduced. Of course, the implant may also have faces which may come into contact with bone. They may, if they are not provided with a biocompatible bone contact layer, be separated from the bone tissue, e.g., by a bone cement layer. In particular, a tibial plate may thus be fixed by means of bone cement on an appropriately prepared bone face of the tibia, facing in the direction of the femur.

The shank of the implant is favorably intended to be anchored in the bone cavity without bone cement. "Is intended" and "the intended purpose", respectively, means in this case that the shank is made of a material or is coated with a material which enables a direct contact with bone tissue, without the undesired side effects described above occurring, as they are known from plastic implants in which plastic is in direct contact with bone tissue. A shank formed in such a way may thus be anchored in the bone cavity without bone cement as a result of the biocompatible bone contact layer, namely without the risk that a connective tissue deformation or partial damage to the shank made of plastic may occur.

It is advantageous if the implant comprises a base body and if the shank extends away from a lower side of the base body. The base body may be configured, e.g., in the form of a tibial plate with sliding faces for abutting against corresponding sliding faces of a femoral component. The shank extending away from the base body serves for an optimized anchoring of the implant on the bone.

In order to further improve a fixing of the implant on the bone, provision may in particular be made for the base body to have a base body bone contact face for abutting against a prepared bone face. Thus, in other words, not only the shank may come into contact with bone tissue, but also the base body or another part of the implant. If the base body bone contact face is not provided with a biocompatible bone contact layer, then the implant may be fixed on the bone by means of bone cement to avoid the disadvantages of a contact of plastics with bone tissue.

It may further be advantageous if the base body bone contact face is provided with a second biocompatible bone contact layer or bears a second biocompatible bone contact layer. This further development allows, in particular, anchoring the implant on the bone entirely without bone cement. The undesired disadvantages described above of a contact of plastics and bone tissue may thus be avoided in a simple manner.

Further, it is favorable if the base body is intended to be anchored on the bone without bone cement. "Is intended" and "the intended purpose", respectively, means here, too, that the base body is made of a material or is coated with a material which enables a direct contact with bone tissue, without the undesired side effects described above occurring, as they are known from plastic implants in which plastic is in direct contact with bone tissue.

The implant may be formed particularly simply if the first bone contact layer and the second bone contact layer are of identical configuration. In particular, they may be applied in one manufacturing step, for example if the implant is formed as one piece, in particular monolithically.

It is advantageous if the first and/or the second bone contact layer have a thickness in a range of about 1 µm to about 1000 µm. In particular, they may have a thickness in a range of about 5 µm to about 700 µm. Forming a bone contact layer with a thickness in the specified range has the advantage that the implant, despite its advantageous property, namely being able to be implanted without bone cement, may be formed particularly easily and/or lightweight. The first and/or the second bone contact layer are preferably at least so thick that a direct bone contact between the plastic from which the implant is made and the bone tissue may be reliably avoided.

In order to improve the ingrowth of bone tissue and, respectively, the growth of bone tissue onto the implant, it is favorable if the first and/or the second bone contact layer are formed rough. They preferably have a roughness in a range of about 0.5 µm to about 10 µm.

In order to be able to form the first and/or the second bone contact layer with a desired roughness, and simultaneously with simple production of the implant, it is advantageous if the bone contact face and/or the base body bone contact face have a roughness in a range of about 0.5 µm to about 10 µm. The respective surfaces of the implant, the intended purpose of which is to come into contact with bone tissue, may then be coated in a simple manner with a thin bone contact layer, wherein the roughness of the bone contact face and/or the base body bone contact face may be maintained or substantially maintained. This may take place, e.g., by applying the bone contact layers by means of cold gas spraying and/or by physical and/or by chemical vapor deposition.

It is favorable if the first and/or the second bone contact layer are made of at least one metal and/or of a biocompatible plastic and/or of a ceramic and/or of at least one bone mineral substance. Depending on the plastic of which the implant is made, the suitable material may be made in order to form the first and/or second bone contact layer.

The at least one metal preferably is titanium or contains titanium. It may thus in particular also be an alloy which contains titanium and other biocompatible metals.

The biocompatible plastic advantageously is or contains polyetheretherketone (PEEK). PEEK is optimally suited in order to form light but nevertheless biocompatible implants, in particular to also coat non-biocompatible plastics.

It may further be favorable if the bone mineral substance is hydroxyapatite. Hydroxyapatite occurs in living beings and arises in particular in the human body through biomineralization. It is contained in bone at a proportion of about 40%. A particularly bone-compatible contact between the bone and the implant may thus be formed.

A coating of the implant made of the plastic may be achieved in a simple manner if the first and/or the second bone contact layer are formed by cold gas spraying and/or by physical and/or by chemical vapor deposition. In particular, thin bone contact layers may thus be formed, for example in the thickness ranges specified above.

The first and/or the second bone contact layer are preferably formed entirely closed. In this way, it may in particular be ensured that bone tissue does not come into contact with the plastic of which the implant is made.

It may further be favorable if the implant, except for the first and/or the second bone contact layer, is made entirely of the bioincompatible plastic. This enables in particular producing the implant and an implant base body defining the same, respectively, of a plastic which has the desired mechanical properties which are required for forming the implant. In particular, it does not have to be considered whether said plastic is biocompatible or not, as a direct contact between the bioincompatible plastic and bone tissue of the patient may be avoided as a result of the first and/or the second bone contact layer.

In particular, for forming sliding faces in joint implants, it is advantageous if the non-biocompatible plastic is polyethylene or ultra high molecular weight polyethylene (UHMWPE). In particular, sliding faces may thus be integrally or monolithically formed with the implant. The number of required parts for an endoprosthesis may thus be minimized in a simple manner.

The implant is favorably formed as one piece. In particular it may be formed monolithically. An implant is to be understood here in particular as an implant base body which has the first and/or the second bone contact layer.

It is favorable if the implant is configured in the form of a first joint component of an artificial joint or joint implant and has at least one joint face. With a second, correspondingly formed joint component, an artificial joint may thus be formed in a simple manner. In particular, the at least one joint face, it could also be two, three, or more, is integrally or monolithically formed with the implant and the implant base body, respectively.

The at least one joint face is preferably formed by the bioincompatible plastic. The plastic may in particular be selected such that its properties are useable in an advantageous manner for forming a joint face which is as low-friction and low-wear as possible. In particular, UHMWPE may be used here.

For forming a knee joint endoprosthesis, it is in particular advantageous if the first joint component is configured in the form of a tibial component. It may alternatively also be configured in the form of a femoral component. Other joints, too, may thus be produced artificially, for example artificial shoulder joints, artificial ankle joints, or artificial hip joints.

Further, the invention relates to a joint implant with a first joint component and at least one second joint component cooperating with the first joint component, wherein at least one of the first joint component and the at least one second joint component are configured in the form of an implant with a shank, which shank is insertible into a bone cavity, which shank is made of a plastic, in particular of a bioincompatible plastic, and defines at least one bone contact face, wherein the bone contact face is provided or coated with a first biocompatible bone contact layer or bears a biocompatible bone contact layer, wherein the shank of the implant is intended to be anchored in the bone cavity without bone cement and wherein the first bone contact layer is formed entirely closed.

The joint implant overall then at least partially also has the advantages described above in conjunction with preferred embodiments of implants.

It is favorable if the joint implant is configured in the form of a knee joint endoprosthesis, if the first joint component is configured in the form of a tibial component, and if the second joint component is configured in the form of a femoral component. A knee joint endoprosthesis may thus be formed in a simple manner, which comprises at least one, in particular two joint components which are configured in the form of advantageous implants described above. Knee joint endoprostheses of that kind are long-lastingly stable and optimally biocompatible. Further, they may have a minimal weight, which improves the patient's becoming accustomed to the artificial joint.

Schematically depicted for example in FIG. 1 is a joint implant, designated with the reference numeral 10, in the form of a knee joint endoprosthesis 12.

The joint implant 10 comprises a first joint component 14 in the form of a tibial component 16 as well as a second joint component 18 in the form of a femoral component 20.

The first joint component 14 has two joint faces 22 which are formed corresponding to two joint faces 24 of the second joint component 18. The joint faces 22 and 24 are intended to abut against each other and may optionally slide on each other and/or roll on each other for forming an artificial joint.

The two joint components 14 and 18 are subsequently also referred to in short as implant 26.

Providing joint faces 22 and 24, respectively, on the implant 26 is not mandatory, at most if two cooperating implants 26 are provided for forming a joint implant 10. It is thus also conceivable to implant one individual implant 26 as a partial replacement of a bone in the body of a human or an animal.

In connection with FIGS. 1 to 3, the structure of the implant 26 in the form of the tibial component 16 is discussed in more detail.

The implant 26 comprises a shank 30 which is insertible into a bone cavity 28 and is made of a plastic. Further, the implant 26 comprises a base body 32, from the lower side 34 of which the shank 30 extends away.

The joint faces 22 are formed on an upper side 36 of the base body 32.

An outer surface 38 of the shank 30 defines a bone contact face 40. The latter is provided or coated with a first biocompatible bone contact layer 42 or bears such a bone contact layer 42.

The base body 32 further has a base body bone contact face 44 for abutting against a prepared bone face 46. For example, the bone face 46 as schematically depicted in FIG. 1 may be concerning a planar surface thereof, formed after a partial resection of a tibia 48.

The base body bone contact face 44 forms the remaining region of the lower side 34 which surrounds the shank 30.

The implant 26 is overall formed as one piece, and it comprises namely an implant base body 50 of a plastic, formed monolithically, for example by injection molding.

The plastic may in particular be concerning a bioincompatible plastic which, in the case of a bone contact, results in the undesired consequences described at the outset. The non-biocompatible plastic may in particular be concerning polyethylene or ultra high molecular weight polyethylene (UHMWPE).

The monolithic implant base body 50 is, as described, provided with the biocompatible bone contact layer 42 only in the region of the shank 30. Said layer has a thickness in a range of about 1 μm to about 1000 μm. In particular, it may have a thickness in a range of about 5 μm to about 700 μm.

Further, the first bone contact layer 42 has a roughness. It may be in a range of about 0.5 μm to about 10 μm.

The bone contact face 40, i.e., a part of the outer surface of the implant base body 50, may also be rough and have a roughness in a range of about 0.5 μm to about 10 μm.

The first bone contact layer 42 may be made, e.g., of a metal, in particular of titanium or an alloy containing titanium or of a biocompatible plastic like, e.g., polyetheretherketone. Alternatively, the bone contact layer 42 may also be made of a ceramic or of a bone mineral substance. The bone mineral substance may in particular be hydroxyapatite.

The first bone contact layer 42 may in particular be formed by cold gas spraying and/or by physical and/or by chemical vapor deposition.

For avoiding a contact between the implant base body 50 and the bone contact face 40 thereof with bone tissue, the first bone contact layer 42 is formed entirely closed.

The base body bone contact face 44 is uncoated. For avoiding a contact with bone tissue, bone cement may be used here for fixing the implant 26. The bone cement then forms a separating layer between the base body bone contact face 44 and the bone tissue and also serves for fixing the implant 26 on the bone.

The monolithic configuration of the implant base body 50 has the advantage that the joint face 22 may be made of the in particular bioincompatible plastic out of which the implant base body 50 is made.

The embodiment of the implant 26 depicted for example in FIGS. 1 to 3 is configured in such a way that the shank 30 is intended to be anchored in the bone cavity 28 without bone cement. This is made possible by the bone contact layer 42 not affecting bone tissue.

A further embodiment of an implant 26 in the form of a first joint component 14, which is configured as tibial component 16, is schematically depicted in FIG. 4. This embodiment differs from the embodiment of the implant 26 depicted in FIGS. 1 to 3 merely in that the base body bone contact face 44 is also coated, namely with a second bone contact layer 52.

The second bone contact layer 52 may in particular be of identical configuration as the first bone contact layer 42. To avoid repetition, reference is made to the properties of the first bone contact layer 42 specified above, like roughness and manner of production.

The second bone contact layer 52 may also be made of the materials described above, which are specified in conjunction with the description of the bone contact layer 42.

Providing the second bone contact layer 52 enables in particular anchoring the base body 32, as intended, on the bone, i.e., in particular on the bone face 46, without bone cerement.

In the two described embodiments of the implant 26, the shank 30 may optionally also be configured in such a way that it, as required, is anchorable in the bone alternatively or additionally with bone cement.

The femoral component 20 may, in a similar manner to the tibial component 16, have a shank for anchoring in a bone cavity of a femur. Here, too, the shank and, as the case may be, a base body of the femoral component 20 may be provided with one or multiple bone contact layers in order to, upon an implantation of the femoral component on the femur without the use of bone cement, avoid a direct contact between the material from which an implant base body of the femoral component is made and surrounding bone tissue.

REFERENCE NUMERAL LIST 10 joint implant
12 knee joint endoprosthesis
14 first joint component
16 tibial component
18 second joint component
20 femoral component
22 joint face
24 joint face
26 implant
28 bone cavity
30 shank
32 base body
34 lower side
36 upper side
38 surface
40 bone contact face
42 first bone contact layer
44 base body bone contact face
46 bone face
48 tibia
50 implant base body
52 second bone contact layer

What is claimed is:

1. An implant, comprising:
    a shank which is insertable into a bone cavity, the shank being made of a plastic, and the shank defining at least one bone contact face, and
    a base body,
    wherein:
        the at least one bone contact face is provided or coated with a first biocompatible bone contact layer or bears a first biocompatible bone contact layer,
        the shank of the implant is intended to be anchored in the bone cavity without bone cement,
        the first biocompatible bone contact layer is formed entirely closed,
        the base body has a base body bone contact face for abutting against a prepared bone face,
        the base body bone contact face is provided with a second biocompatible bone contact layer or bears a second biocompatible bone contact layer,
        the second biocompatible bone contact layer has a thickness in a range of about 1 µm to about 1000 µm,
        the second biocompatible bone contact layer has a roughness in a range of about 0.5 µm to about 10 µm,
        the implant is configured in the form of a first joint component of an artificial joint implant and has at least one joint face, the at least one joint face for interacting with a corresponding at least one joint face of an at least one second joint component,
        the first joint component is configured in the form of a tibial component of a knee joint endoprosthesis,
        the implant is formed monolithically;
        the first biocompatible bone contact layer is made of a biocompatible plastic; and
        the second biocompatible bone contact layer is made of the biocompatible plastic.

2. The implant in accordance with claim 1, wherein the shank extends away from a lower side of the base body.

3. The implant in accordance with claim 1, wherein the base body is intended to be anchored on the prepared bone face without bone cement.

4. The implant in accordance with claim 1, wherein the implant is intended to be anchored on the bone without bone cement.

5. The implant in accordance with claim 1, wherein the first biocompatible bone contact layer and the second biocompatible bone contact layer are of identical configuration.

6. The implant in accordance with claim 1, wherein at least one of:
    a) the first biocompatible bone contact layer has a thickness in a range of about 1 µm to about 1000 µm,
    b) the first biocompatible bone contact layer has a roughness in a range of about 0.5 µm to about 10 µm, and
    c) at least one of the at least one bone contact face and the base body the base body bone contact face have a roughness in a range of about 0.5 µm to about 10 µm.

7. The implant in accordance with claim 1, wherein the biocompatible plastic is or contains polyetheretherketone (PEEK).

8. The implant in accordance with claim 1, wherein the first biocompatible bone contact layer is formed at least one of by cold gas spraying and by physical vapor deposition and by chemical vapor deposition.

9. The implant in accordance with claim 1, wherein the second biocompatible bone contact layer is at least one of:
    a) is formed entirely closed, and
    b) is formed by at least one of cold gas spraying, physical vapor deposition, and chemical vapor deposition.

10. The implant in accordance with claim 1, wherein at least one of:

a) the implant, except for the first biocompatible bone contact layer and the second biocompatible bone contact layer, is made entirely of a bioincompatible plastic, and b) the implant, except for the first biocompatible bone contact layer and the second biocompatible bone contact layer, is made entirely of a bioincompatible plastic, and the bioincompatible plastic is polyethylene or ultra high molecular weight polyethylene.

11. The implant in accordance with claim 10, wherein the at least one joint face is formed by the bioincompatible plastic.

12. The implant in accordance with claim 1, wherein the implant, except for the first biocompatible bone contact layer and the second biocompatible bone contact layer, is made entirely of a bioincompatible plastic.

13. A joint implant, comprising:
a first joint component and at least one second joint component cooperating with the first joint component, wherein at least one of the first joint component and the at least one second joint component are configured in the form of an implant with a base body and a shank, the shank being insertable into a bone cavity, wherein:

the shank is made of a plastic and defines at least one bone contact face, the at least one bone contact face is provided or coated with a first biocompatible bone contact layer or bears a first biocompatible bone contact layer, the shank is intended to be anchored in the bone cavity without bone cement, the first biocompatible bone contact layer is formed entirely closed, the base body has a base body bone contact face for abutting against a prepared bone face, the base body bone contact face is provided with a second biocompatible bone contact layer or bears a second biocompatible bone contact layer, the second biocompatible bone contact layer has a thickness in a range of about 1 μm to about 1000 μm, the second biocompatible bone contact layer has a roughness in a range of about 0.5 μm to about 10 μm, the joint implant is configured in the form of a knee joint endoprosthesis, the first joint component is configured in the form of a tibial component, the at least one second joint component is configured in the form of a femoral component, the first joint component and the at least one second joint component each comprise interacting joint faces, at least one of the first joint component and the at least one second joint component is formed monolithically;

the first biocompatible bone contact layer is made of a biocompatible plastic; and the second biocompatible bone contact layer is made of the biocompatible plastic.

14. The implant in accordance with claim 13, wherein the first biocompatible bone contact layer has a thickness in a range of about 1 μm to about 1000 μm.

15. The implant in accordance with claim 13, wherein the first biocompatible bone contact layer has a roughness in a range of about 0.5 μm to about 10 μm.

16. The implant in accordance with claim 13, wherein:
the shank extends away from a lower side of the base body, and at least one of the at least one bone contact face and the base body bone contact face have a roughness in a range of about 0.5 μm to about 10 μm.

* * * * *

UNITED STATES PATENT AND TRADEMARK OFFICE
CERTIFICATE OF CORRECTION

PATENT NO. : 11,304,810 B2  
APPLICATION NO. : 16/256016  
DATED : April 19, 2022  
INVENTOR(S) : T. Hagen et al.

Page 1 of 1

It is certified that error appears in the above-identified patent and that said Letters Patent is hereby corrected as shown below:

On the Title Page

"(73) Assignee: Aesculap AQ, Tuttlingen (DE)" should read -- (73) Assignee: Aesculap AG, Tuttlingen (DE) --

In the Claims

Column 8, Line 49: "base body the base body bone contact face have a" should read -- base body bone contact face have a --

Signed and Sealed this  
Twelfth Day of July, 2022

Katherine Kelly Vidal  
*Director of the United States Patent and Trademark Office*